United States Patent [19]

Jessup

[11] 4,405,322
[45] Sep. 20, 1983

[54] ANESTHESIA DEVICE

[75] Inventor: James L. Jessup, Elk Grove Village, Ill.

[73] Assignee: The Kendall Company, Boston, Mass.

[21] Appl. No.: 334,030

[22] Filed: Dec. 23, 1981

[51] Int. Cl.³ .............................................. A61M 5/00
[52] U.S. Cl. .................................. 604/232; 604/240; 604/283
[58] Field of Search ................. 604/93, 187, 191, 218, 604/232, 239, 280, 283, 240

[56] References Cited

U.S. PATENT DOCUMENTS

| | | | |
|---|---|---|---|
| 1,234,582 | 7/1917 | Trueblood | 604/191 |
| 3,399,668 | 9/1968 | Lundgren | 604/283 X |
| 4,112,945 | 9/1978 | Helixson et al. | 604/232 X |
| 4,182,326 | 1/1980 | Ogle | 604/232 X |

*Primary Examiner*—Dalton L. Truluck
*Attorney, Agent, or Firm*—Powell L. Sprunger

[57] ABSTRACT

An anesthesia device comprising, a syringe having a barrel defining a chamber, a hollow needle at a distal end of the syringe, and a plunger for pumping fluid from the chamber through the needle. The device has a holding member having a wall with an inner diameter slightly larger than the outer diameter of the syringe barrel, an open proximal end, and an opening at a distal end of the holding member, with the wall defining a cavity to receive the syringe barrel. The device has an elongated cannula having a lumen, and a plurality of apertures in a distal portion of the cannula communicating with the lumen. The device has a hollow adapter secured to a proximal end of the cannula. The adapter receives a distal portion of the syringe with the needle received in the cannula lumen, and the holding member receives the syringe and attached cannula with the syringe barrel received in the holding member cavity, and with the cannula extending distally from the holding member opening. Alternatively, the holding member receives the syringe while the cannula is unattached to the syringe with the syringe barrel received in the holding member cavity, and with the syringe needle extending distally from the holding member opening.

5 Claims, 5 Drawing Figures

ANESTHESIA DEVICE

CROSS REFERENCE TO RELATED APPLICATION

Application Ser. No. 230,912 filed Feb. 2, 1981, now abandoned.

BACKGROUND OF THE INVENTION

The present invention relates to anesthesia devices.

Before the present invention, it has been a common practice to apply an anesthetic drug to the trachea of a patient prior to endotracheal intubation or bronchoscopy. There have been two procedures to accomplish this result. For a laryngotracheal procedure, a cannula is inserted down the throat into the trachea. Alternatively for a transtracheal procedure, a needle is passed through the anterior tracheal wall. The transtracheal procedure is undertaken when the laryngotracheal procedure cannot be accomplished, and some physicians have preferences between the two procedures. In the past, the two procedures have required different devices in order to carry out the separate procedures.

SUMMARY OF THE INVENTION

A principal feature of the present invention is the provision of an improved anesthesia device of simplified construction.

The anesthesia device comprises, a syringe having a barrel defining a chamber, a hollow needle at a distal end of the syringe, and means for pumping fluid from the chamber through the needle. The device has a holding member having a wall with an inner diameter slightly larger than the outer diameter of the syringe barrel, an open proximal end, and an opening at a distal end of the holding member, with the wall defining a cavity to receive the syringe barrel. The device also has an elongated cannula having a lumen, and a plurality of apertures in a distal portion of the cannula communicating with the lumen. The device has a hollow adapter secured to a proximal end of the cannula.

A feature of the present invention is that the adapter receives a distal portion of the syringe with the needle received in the cannula lumen, and the holding member receives the syringe and attached cannula with the syringe barrel received in the holding member cavity, and with the cannula extending distally from the holding member opening.

Thus, a feature of the present invention is that the device may be assembled for use in a laryngotracheal procedure.

Another feature of the invention is that the device prevents loss of the cannula down the patient's throat.

Yet another feature of the invention is that the holding member receives the syringe while the cannula is unattached to the syringe with the syringe barrel received in the holding member cavity, and with the syringe needle extending distally from the holding member opening.

Thus, another feature of the invention is that the device may be assembled for a transtracheal procedure.

Accordingly, a feature of the present invention is that the single device may be assembled alternatively for a laryngotracheal procedure or a transtracheal procedure.

Further features will become more fully apparent in the following description of the embodiments of this invention and from the appended claims.

DESCRIPTION OF THE PREFERRED EMBODIMENTS

Figure 1:
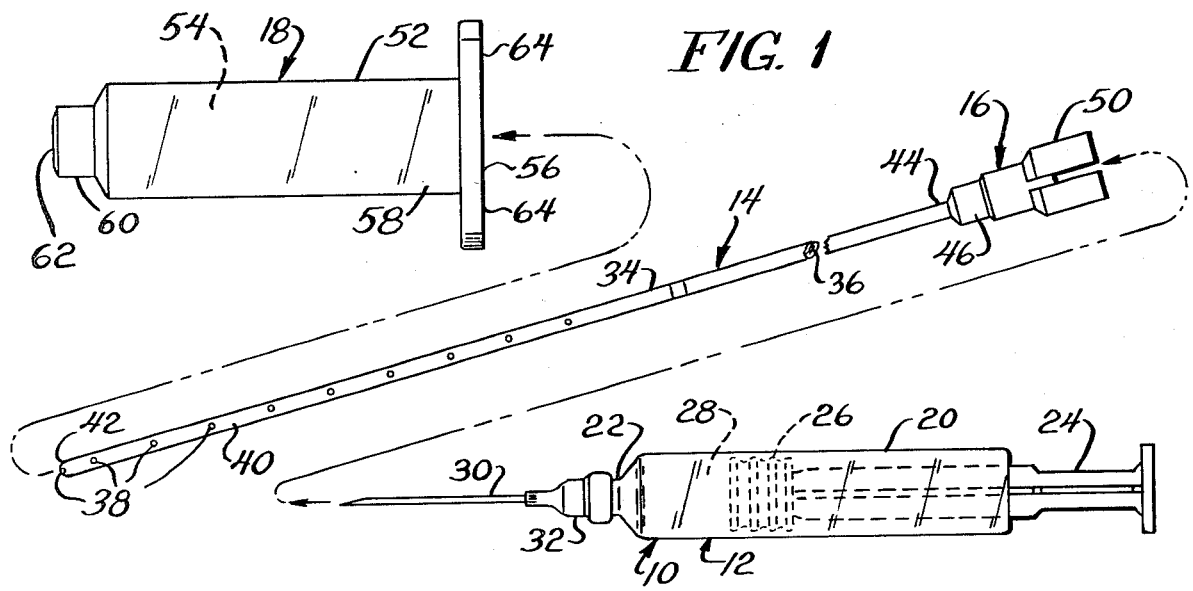
FIG. 1 is an exploded fragmentary plan view of an anesthesia device of the present invention comprising a syringe, a cannula, an adapter, and a holding member.
Figure 4:
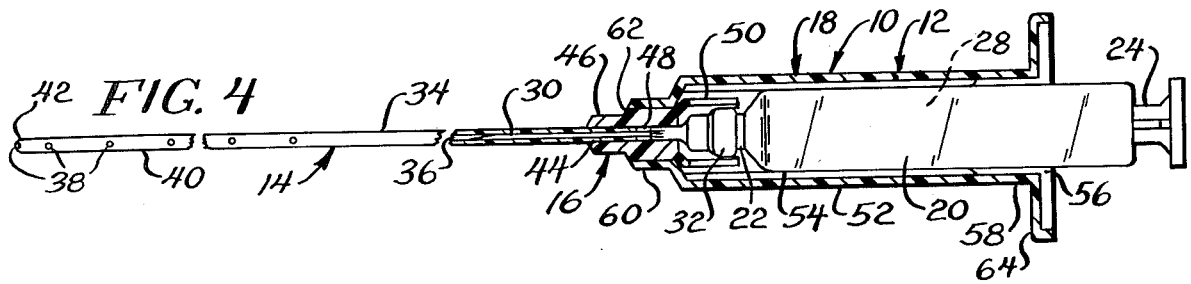
FIG. 4 is a fragmentary plan view taken partly in section of the assembled device of FIG. 3.

Referring now to FIGS. 1 and 4, there is shown an anesthesia device generally designated 10 comprising a syringe 12, an elongated cannula 14, an adapter 16, and a holding member 18. The syringe 12 may be of the type comprising a hollow cylindrical barrel 20 defining a chamber 28, a tip 22 extending distally from the barrel 20, and a plunger 24 received in the barrel 20, with the plunger 24 having a distal head 26 of elastic material, such as rubber, received in the chamber 28 of the barrel 20 and engaging against an inner surface of the barrel 20. The syringe 12 has an elongated distal hollow needle 30, and a hub 32 securing a proximal end of the needle 30 to the tip 22 of the syringe 12. In use, the syringe plunger 24 is pumped in order to eject a liquid anesthetic drug from the chamber 28 through the distal needle 30.

The cannula 14 has a hollow wall 34 defining a lumen 36, and a plurality of apertures 38 in a distal portion 40 and at the distal end 42 of the cannula 14 communicating with the lumen 36. The cannula 14 has a proximal end 44 attached to the adapter 16. The cannula 14 may be made of a suitable material, such as plastic.

The adapter 16 has a hollow distal tongue 46 defining a bore 48 which receives and securely engages the proximal end 44 of the cannula 14. The adapter 16 also has a proximal annular flange 50 for a purpose which will be described below.

The holding member 18 has a cylindrical wall 52 defining a cavity 54. The inner diameter of the wall 52 is slightly larger than the outer diameter of the syringe barrel 20, such that the syringe barrel 20 may be received in the cavity 54 of the holding member 18. The holding member 18 has an opening 56 at a proximal end 58 of the holding member 18, and an annular shoulder 60 of reduced diameter extending distally from the wall 52, with the shoulder 60 defining a distal opening 62. Also, the holding member 18 has an outwardly directed flange 64 at the proximal end 58 of the wall 52 defining finger grips for the holding member 18. As shown in FIG. 4, the flange 50 of the adapter 16 has a larger diameter than the inside diameter of the shoulder 60 of the holding member 18.

Figure 2:
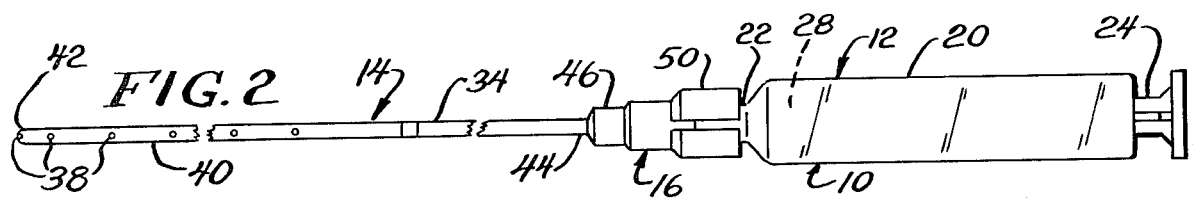
FIG. 2 is a fragmentary plan view showing the syringe attached to the adapter on the cannula.
Figure 3:
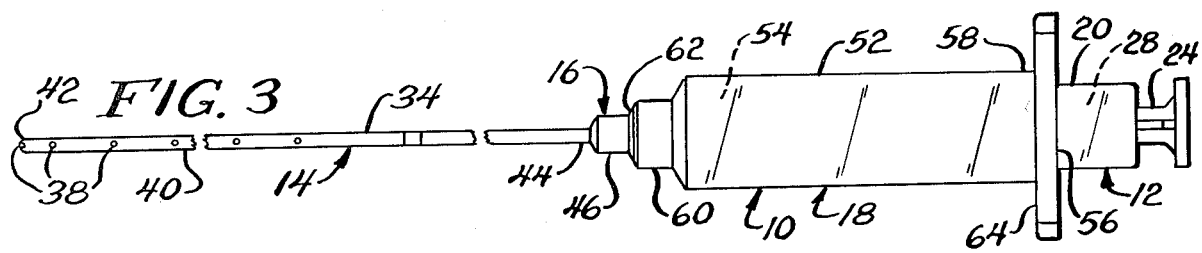
FIG. 3 is a fragmentary plan view of the device showing the syringe and cannula inserted into the holding member for a laryngotracheal procedure.

With reference to FIGS. 1 and 2, in use of the device 10 for a laryngotracheal procedure, the needle 30 of the syringe 12 is inserted through the adapter 16 into the lumen 36 of the cannula 14, with the syringe hub 32 being received in the adapter 16. Next, with reference to FIGS. 3 and 4, the attached cannula 14 and syringe 12 are inserted into the cavity 54 of the holding member 18 until the holding member shoulder 60 snugly receives the adapter 16. In this configuration, the cannula 14 extends distally from the opening 62 of the holding member 18, with the syringe barrel 20 being received in the holding member cavity 54. As shown in FIG. 4, the flange 50 of the adapter 16 engages against an inner portion of the holding member shoulder 60 in order to releasably hold the adapter 16 and cannula 14 in place. In this assembled configuration, the distal portion 40 of the cannula 14 is inserted down the patient's throat, and the syringe 12 is pumped in order to eject an anesthetic drug from the syringe chamber 28 through the needle 30 and cannula apertures 38 onto the trachea of the patient preparatory to an endotracheal intubation or bronchoscopy. The proximal end 44 of the cannula 14 is firmly held in the adapter 16 in order to prevent loss of the cannula 14 down the patient's throat during the laryngotracheal procedure.

Figure 5:
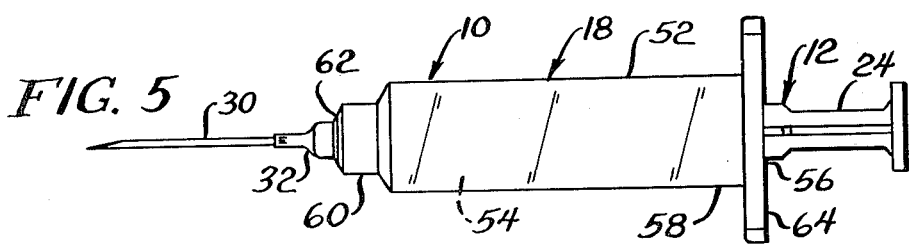
FIG. 5 is a plan view illustrating the syringe received in the holding member for a transtracheal procedure.

Alternatively, with reference to FIG. 5, for a transtracheal procedure the syringe 12 may be inserted into the holding member 18 while the cannula 14 is unattached to the syringe 12. In this configuration, the hub 32 of the syringe 12 is received in the holding member shoulder 60 with the syringe needle 30 extending distally from the holding member opening 62, and with the syringe barrel 20 received in the holding member cavity 54. In the assembled configuration of the device 10, the needle 30 of the syringe 12 is passed through the anterior tracheal wall of the patient while the flange 64 serves as a finger grip for the physician, and the syringe 12 is then pumped in order to eject an anesthetic drug from the syringe chamber 28 through the neele 30 into the trachea of the patient preparatory to endotracheal intubation or bronchoscopy.

Thus, in accordance with the present invention, the anesthesia device 10 may be assembled in a simplified fashion for use in either a laryngotracheal procedure or a transtracheal procedure, as desired by the physician.

The foregoing detailed description is given for clearness of understanding only, and no unnecessary limitations should be understood therefrom, as modifications will be obvious to those skilled in the art.

I claim:

1. An anesthesia device, comprising:
   a syringe having a barrel defining a chamber, a hollow needle at a distal end of the syringe and having a sharp distal end, and means for pumping fluid from the chamber through said needle;
   a holding member having a wall with an inner diameter slightly larger than the outer diameter of the syringe barrel, an open proximal end, and an opening at a distal end of the holding member, with said wall defining a cavity to receive the syringe barrel;
   an elongated cannula having a lumen, and a plurality of apertures in a distal portion of the cannula communicating with said lumen; and
   a hollow adapter secured to a proximal end of the cannula, said adapter receiving a distal portion of the syringe with the needle received in the cannula lumen, and said holding member receiving the syringe and attached cannula with the syringe barrel received in the holding member cavity, with the cannula extending distally from the holding member opening, and with the adapter releasably received in the holding member.

2. The device of claim 1 wherein the holding member has a distal annular shoulder defining said opening.

3. The device of claim 2 wherein the adapter has a proximal annular flange, with said flange having a larger diameter than the inside diameter of said shoulder, such that the flange engages against the shoulder when the cannula is fully inserted into the holding member.

4. The device of claim 1 wherein said syringe has a distal tip, and including a hub securing the needle to said tip, said hub extending through the holding member opening when the syringe only is fully inserted into the holding member.

5. The device of claim 1 wherein said holding member has an outwardly directed flange at a proximal end of the holding member.

* * * * *